United States Patent [19]

Orlando

[11] 4,024,752
[45] May 24, 1977

[54] METHOD AND APPARATUS FOR SIMPLE FIELD TEST TO DETERMINE FINAL BOILING POINT OF A VOLATILE LIQUID SAMPLE

[75] Inventor: Matthew R. Orlando, Princeton, N.J.

[73] Assignee: Mobil Oil Corporation, New York, N.Y.

[22] Filed: July 12, 1976

[21] Appl. No.: 704,862

[52] U.S. Cl. .................................. 73/17 A; 73/231
[51] Int. Cl.² ................. G01N 25/08; G01N 31/08
[58] Field of Search ................. 73/17 A, 23.1, 61.1

[56] References Cited
UNITED STATES PATENTS

| | | | |
|---|---|---|---|
| 3,169,389 | 2/1965 | Green, Jr. et al. | 73/23.1 X |
| 3,183,515 | 5/1965 | Hartman et al. | 73/23.1 X |
| 3,232,093 | 2/1966 | Burow et al. | 73/23.1 |

*Primary Examiner*—Herbert Goldstein
*Attorney, Agent, or Firm*—Charles A. Huggett; Raymond W. Barclay; Thomas S. Szatkowski

[57] ABSTRACT

An apparatus is provided to directly measure the retention time of a volatile liquid sample in the column of a chromatograph. The apparatus is characterized by a chromatograph having certain resolution, a timer, and a circuit to activate the timer while the sample is eluted from the column.

A simple field test to determine the final boiling point of a hydrocarbon fraction such as gasoline is effected by comparing the retention time found for an unknown sample with that of a sample having known final boiling point.

10 Claims, 5 Drawing Figures

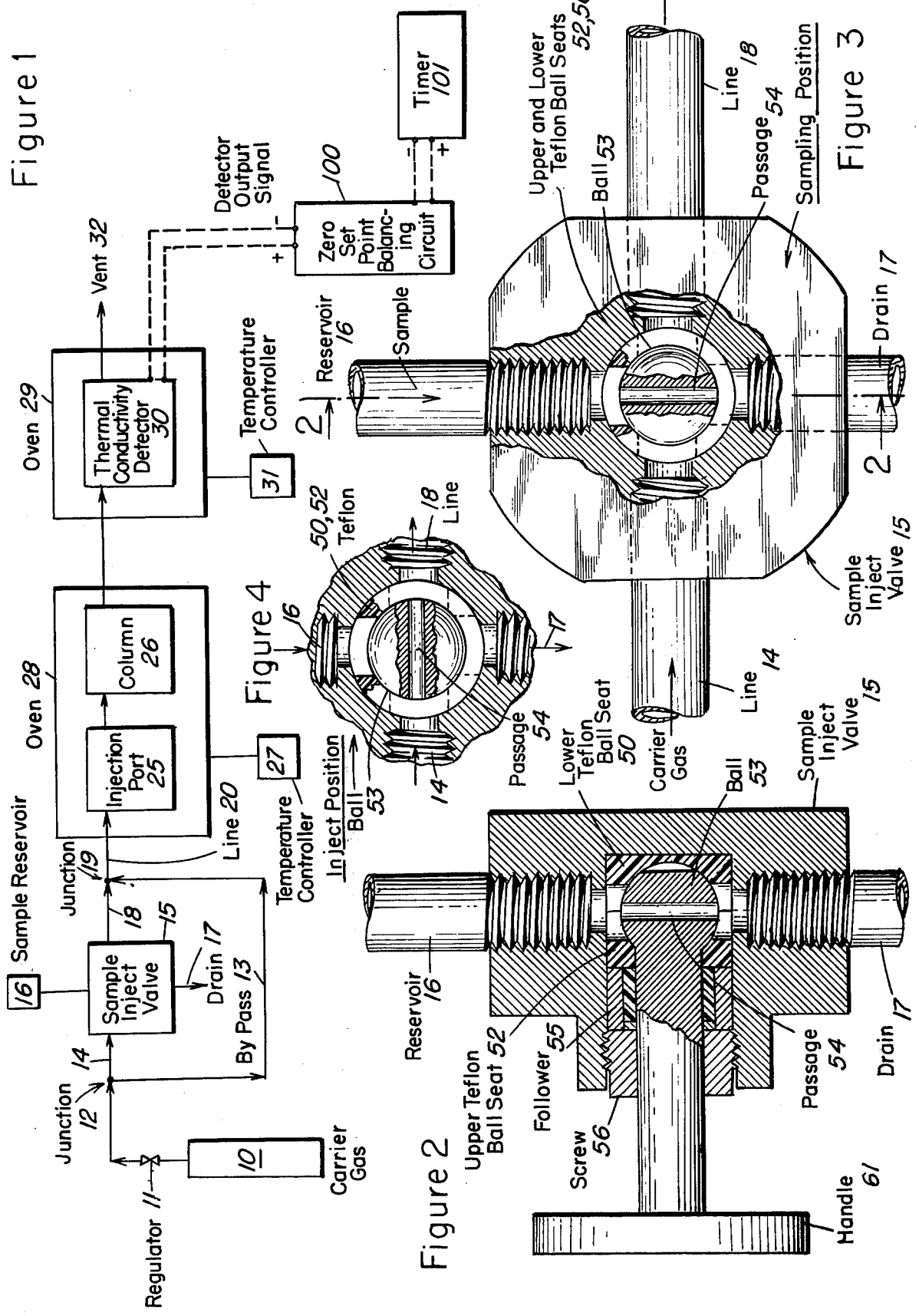

METHOD AND APPARATUS FOR SIMPLE FIELD TEST TO DETERMINE FINAL BOILING POINT OF A VOLATILE LIQUID SAMPLE

BACKGROUND OF THE INVENTION

1. Field of the Invention

The invention relates to a gas-liquid chromatographic apparatus and a quick, accurate field test method for determining the final boiling point of a gasoline or other volatile liquid fraction.

2. Description of the Prior Art

Petroleum products, among others, must meet certain specifications before they can be marketed. An important specification, which is strictly enforced by Federal and State law, pertains to the final boiling point of the product and takes the form of an upper limit. The importance can be readily understood by considering that the Final Boiling Point of a product such as gasoline will markedly change if the gasoline becomes contaminated with other products such as kerosene or diesel fuels. The possibility of contamination exists since gasoline is distributed by pipeline, which may have previously been used to transport other products. Thus, certification that a gasoline meets specifications at a refinery exit, for example, does not insure that the product will meet specifications at the point of sale.

Current experimental methods used for the determination of the final boiling point of petroleum fractions employ distillation, however, simulated distillations such as by chromatographic means are also used. Interestingly, both of these methods are directed toward producing the entire boiling point distribution of the product, rather than just determining the final boiling point.

A method for the determination of the boiling distribution of a petroleum product by actual distillation is described by ASTM test D86-67. Briefly, a sample of the product is distilled under prescribed conditions and systematic observations of thermometer readings and volumes of condensate are made. The boiling point distribution must then be calculated from the observed readings.

Chromatography, which is also used to produce boiling point distributions, can be broadly defined as a technique for the separation and identification of chemical compounds. More specifically, it may be described as a process in which the components of a mixture are separated from one another by volatilizing a sample of the mixture into a carrier gas stream which is passed through and over a bed of packing generally comprising a 20 to 200 mesh solid support. The surface of the solid support is usually coated with relatively nonvolatile liquid, giving rise to the term gas-liquid chromatography. Different components move through the bed at different rates and so appear one after another at the effluent end of the bed where they are detected and measured by thermal conductivity changes, density differences or ionization detectors.

Methods for the determination of boiling point distributions by chromatography are described by ASTM test D2887-73 or U.S. Pat. No. 3,169,389. Briefly, the methods involve using: a chromatograph to resolve an unknown mixture of compounds into fractions having similar boiling points; a recorder to produce a graphical representation of the amount of each fraction as detected by a suitable means; and an integrator to produce a record of the cumulative amount of each of the fractions. Boiling point temperatures are assigned at various intervals as determined by previous experiment using a standard mixture containing materials of known boiling point. As presently practiced, these chromatographic methods are capable of producing a boiling point distribution, however they require the use of sophisticated equipment and techniques. Gas-liquid chromatographic columns and detectors must be capable of certain resolution, columns must be temperature programmed at reproducible rates, certain peaks must be identified, and precise calculations must be made.

It is readily observed that due to the complexity of the above mentioned methods for the determination of boiling point distributions, they are considered to be unsuitable for use in any environment other than a well-equipped laboratory. Thus, since final distribution terminals or points of sale of petroleum products are not usually characterized as containing such facilities, the need exists for a simple test which can be used outside of the laboratory to find the final boiling point of volatile hydrocarbon fractions.

SUMMARY OF THE INVENTION

Therefore, in accordance with one aspect of the invention, a simple and portable gas-liquid chromatographic apparatus is provided for the determination of the final boiling point of a volatile liquid sample. The apparatus is characterized by:

a. a chromatograph of such resolution that the detector output signal exceeds a set point, hereinafter defined, during the elution of at least 98% of said sample from the column;

b. a timer; and c. means for energizing the timer during the period in which the detector output signal exceeds the set point, said set point being greater then signals resulting from instrument and line noise, and less than the detector output signal during the elution of at least 98% of the sample from the column of the chromatograph.

As will be described in more detail hereinafter the chromatograph of the present invention is generally described as including:

a. a chromatographic column;

b. means for creating a continuous flow of carrier gas through the column;

c. means for injecting a measured amount of a volatile liquid sample into the flow of carrier gas;

d. means for volatilizing said sample prior to entry into the column; and e. means for detecting said sample eluted from the column.

The column characteristics and operation conditions of the gas chromatograph are preferably chosen such that individual boiling fractions or components thereof are not separately resolved, as in the prior art, but are instead eluted in one large peak.

In accordance with another aspect of the invention, the apparatus described herein used to effect a simple field test for the determination of the final boiling point of a volatile hydrocarbon sample by comparing the retention time found for a sample having known final boiling point. The term volatile hydrocarbon fraction is used to include samples such as gasoline, kerosine, gas oils and the like and to exclude samples such as heavy crude oils, resids, asphalts and the like.

If the sample having known final boiling point is chosen such that its final boiling point is the same as the current upper boiling limit specified by law, then a futher simplified pass-fail test can be effected. A gasoline sample fails the test and does not meet the legal specification if its retention time is higher than that of the chosen sample with known final boiling point. The gasoline sample would pass if its retention time were lower than that of the known sample.

Thus the apparatus and method of the present invention provides a simple test which can be used outside of the laboratory for investigations where compliance with final boiling point specifications is involved.

BRIEF DESCRIPTION OF THE DRAWINGS

FIG. 1 is a diagrammatic representation of a specific embodiment of the present invention with various components shown in block form;

FIG. 2 is a section view taken along line 2—2 of FIG. 3;

FIG. 3 is a fragmentary view of an automatic inject valve suitable for a specific embodiment of the invention;

FIG. 4 is a view similar to FIG. 3, but with the ball of the valve in the inject position;

DESCRIPTION OF SPECIFIC EMBODIMENTS

Figure 5:
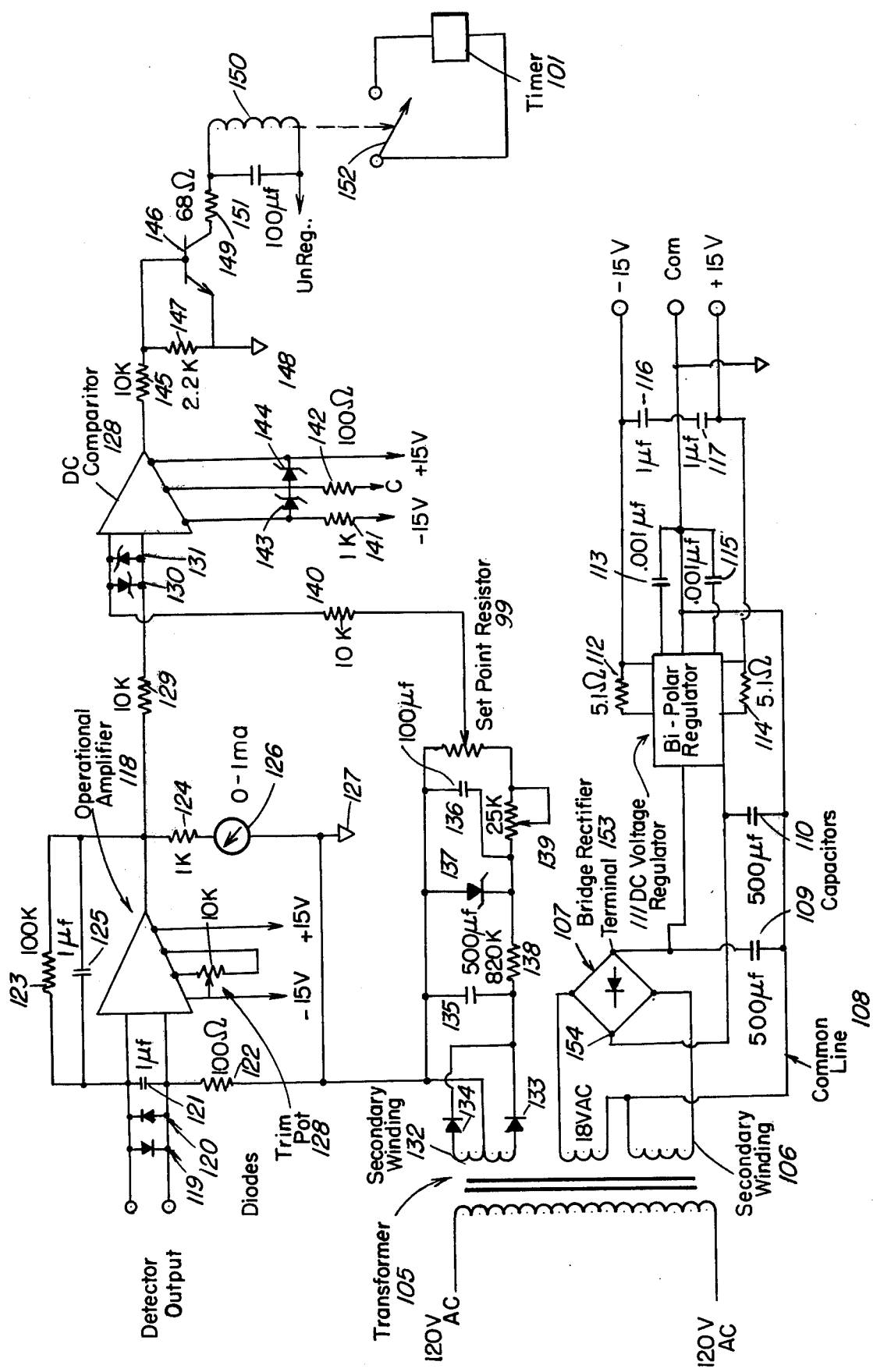
FIG. 5 shows a zero set point circuit suitable for a specific embodiment of the invention.

With reference to FIG. 1, carrier gas, which may be helium, nitrogen or $CO_2$, but is preferably helium, is fed from a cylinder or other suitable source 10 through regulator 11 at a flow of about 5 to about 10 liters/hr. with the preferred range being from about 8.5 to about 10 liters/hr. At junction 12 the flow is split, part entering line 14 and part using bypass line 13 to enter injection port 25 via junction 19 and line 20. Sample inject valve 15 is bypassed in this manner, except when a sample is injected as will be described.

Line 14 is connected to sample inject valve 15, which may be described by referring to FIG. 2. Sample reservoir 16 and drain 17 are connected to valve 15 as shown. Valve 15 is known as a ball type valve and comprises a ball 53 having a certain size passage 54 drilled through. Ball 53 is seated between upper and lower polymerized tetrafluoro ethylene seats 52 and 50, respectively, which are held in contact with ball 53 by follower 55 and screw 56. The contact provided is enough to prevent leakage, however, ball 53 may be rotated freely by handle 61.

Referring now to FIG. 3, it is seen that the valve is placed in the sampling position when passage 54 of ball 53 is held vertically so that sample from reservoir 16 may be pulled downward by gravity and flow through passage 54 into drain 17. After an amount of time has passed so that the sample flowing through passage 54 is considered to be representative of the sample in reservoir 16, ball 53 may be rotated to the position shown in FIG. 4. Carrier gas from line 14 now flows through passage 54 and pushes the sample which is trapped in the passage into line 18. This line leads to junction 19 where the sample and carrier gas are mixed with bypassed carrier gas before entering injection port 25 from line 20. The sample is vaporized in the injection port before being carried into column 26. In the analysis of gasoline range materials, for example, passage 54 of valve 15 is sized so that a 6 microliter sample is injected into injection port 25. In some aspects, sample valve 15 may be similar to the valve in U.S. Pat. No. 3,475,950.

Injection port 25 is similar to conventional injection ports used in chromatography. Of course, the prior art hypodermic syringe and septum method of injecting samples has been eliminated in this embodiment, however, it may be desirable to use the prior art method in certain situations.

Returning to FIG. 1, it is shown that both injection port 25 and column 26 may be located in oven 28 which is well insulated and kept at an isothermal temperature by temperature controller 27 operating a cartridge-type heater, not shown. Column 26 may be one of many chromatographic columns known in the art, such as capillary or gas-liquid. Gas-liquid chromatographic columns which comprise a hollow tube packed with a solid support, the surface of which is coated with a non-volatile liquid, especially those columns of low resolution, are preferred. The non-volatile liquid phase should be stable at the temperature employed in the operation of the apparatus. A particularly preferred material may be a silicone rubber gum, which is a viscous, high boiling dimethyl silicone polymer. A material such as G.E. No. SE-30 Silicone Rubber Gum, marketed by General Electric Company is particularly preferred. The solid support may be described as a solid phase which partitions the sample by absorption and selectively releases the sample by boiling range or dielectric constant i.e., polarity of the sample. This is a support media for the liquid phase but does perform some degree of separations, although the amount is not completely known. A particularly preferred support is Gas Chrom W, marketed by Applied Science, College Park, Pa.

The column may comprise various lengths and packings, as is known in the art. However, a four foot long, ¼ inch diameter stainless steel tube packed with 5%, by weight, SE-30 Silicone Rubber gum coated on gas Chrom. W., which is sized to 80–100 mesh, was found to be most effective. Another usable column is 5%, by weight, DC-200 silicon oil coated on Gas Chrom. Q, which is sized to 80–100 mesh. One skilled in the art would be aware of other columns which could be effectively utilized herein.

The column is preferably maintained at an isothermal temperature. In the analysis of gasoline range materials, the temperature is selected from the range of about 250° F to 350° F. This temperature range is dependent on column length and conditioning of the column. If the column were used for analyzing higher boiling hydrocarbons, it may have greater retention characteristics, thus requiring a higher temperature for optimum performance.

As the sample elutes from column 26, it continues into detector 30 which may be one of many known in the art, but in a specific embodiment is a thermal conductivity detector of flow through design with two rhenium tungsten filaments on standard mounts. The detector 30 is located in oven 29, which is insulated and maintained isothermally by temperature controller 31 operating on a heater, not shown. After the sample passes through the thermal conductivity detector, it is discarded through vent 32. The output of the thermal conductivity detector is an electronic signal of 0–1 miliamps, and is connected to the zero set point balancing circuit 100, which is used to activate timer 101. This will be described presently.

In general, the operation of the zero set point balancing circuit 100 is as follows: the circuit senses the output of the thermal conductivity detector and compares the magnitude of the output signal with that of a set point signal which may be adjusted by variable resistor 99. Thus, when the magnitude of the detector output is greater than the chosen set point signal, a relay is activated. This relay provides power for timer 101, which may be of any type known in the art but is preferred to be a 120 volt AC type with digital readout in tenths of a minute. When the magnitude of detector output is less than the chosen set point signal, the relay is open and timer 101 is stopped. The set point signal is adjusted to be small enough so that 98% of the sample injected is eluted from the column before timer 101 has been stopped, however, it also must be high enough to eliminate the possibility of measuring instrument on line noise.

Referring now to FIG. 5, which depicts circuit 100, it is seen that 120 V AC is supplied to the primary winding of step down transformer 105. Secondary winding 106 is thus provided with 18 V AC and is connected to bridge rectifier circuit 107. The bridge rectifier circuit 107 develops −15 volt DC between the right-hand terminal 153 and a common line 108, connected to the center tap of winding 106; and a +15 volt DC between the left-hand terminal 154 of bridge 107 and the common line. The DC output of the rectifier circuit is connected through a circuit which consists of capacitors 109 and 110 to DC voltage regulator 111. A regulator suitable for use herein is Motorola MC 15686. The regulator 111 is connected to the circuit which consists of resistor 112 and capacitor 113 for the negative side and resistor 114 and capacitor 115 for the positive side. Thus, a regulated −15 V DC is developed across capacitor 116 and a regulated +15 V DC is developed across capacitor 117.

The detector output is connected to operational amplifier 118. Diodes 119, 120 and capacitor 121 are provided for fault protection, i.e., to automatically limit the amplifier input voltage. The amplifier is connected to the +15 V and −15 V DC regulated power supply, previously described. Feedback resistor 123, resistors 122 and 124; feedback capacitor 125 and meter 126 are connected to ground connection 127. Variable resistor 128 provides a zero control to minimize the temperature drift of the amplifier. The output of amplifier 118 is a signal of 0–1 volts which varies directly with the 0–1 milliamp input signal. This output signal is connected via resistor 129 to DC comparator 128.

Secondary winding 132 of transformer 105 is provided with 18 V AC and is connected across diodes 133 and 134 to a series parallel circuit which consists of capacitors 135 and 136, zener diode 137, resistor 138 and variable resistors 139 and 99. Variable resistor 139 is used as a calibration device. Variable resistor 99 is used to adjust the set point signal hereinbefore described. Thus the output of the series parallel circuit is the DC set point signal, which varies between 0–1 volts.

The set point signal is connected to DC comparator 128 across resistor 140. Zener diodes 130 and 131 are provided for fault protection. Comparitor 128 is connected to the −15 V and +15 V regulated power supply through resistors 141 and 142 and zener diodes 143 and 144. Comparator 128 generates an output signal across resistor 145 only if the output signal of amplifier 118 is greater than the set point signal. Resistor 145 is connected to transistor amplifier circuit which consists of transistor 146, resistor 147 and group 148. The output of this circuit energizes a relay which consists of resistor 149, induction coil 150 and capacitor 151.

When the relay is energized normally open switch 152 is closed, thus activating timer 101.

The apparatus described hereinabove was set in the following mode, which is the preferred mode for testing gasoline range samples:

| GAS CHROMATOGRAPHIC OPERATING CONDITIONS | |
|---|---|
| Column diameter | 1/4" Stainless Steel tubing |
| Column length | 4 feet |
| Liquid | Silicon gum rubber |
| Percent liquid phase | 5 weight percent |
| Support material | Gas Chrom. W |
| Size | 80/100 mesh |
| Column and injection port temperature | 160° C |
| Carrier gas | Helium |
| Gas flow | 10 l/hr |
| Detector | Thermal conductivity |
| Detector temperature | 160° C |
| Sample Size | 6 microliters |
| Set point | Adjusted to energize timer at detector outputs above 0.01 milliamps |

The apparatus may be set differently to test volatile petroleum fractions other than gasoline as those skilled in the art will readily understand. Thus, it will be possible to test for the final boiling point of kerosenes, gas oils, motor oils and the like.

EXAMPLE 1

A simple pass-fail test is effected by injecting a sample with a known final boiling point of 437° F into the apparatus which is set in the mode described herein above and recording the retention time found for that sample. The timer is reset and the same procedure is followed with the injection of a sample of unknown final boiling points. In this case samples boiling at 400° and 473° F were used as "unknowns" A and B. The test results are shown in Table 1.

Table 1

| | Simple Pass Fail Test Results | | |
|---|---|---|---|
| Sample Number | Retention Time for Sample having 437° F Final Boiling Point, Minutes | Retention Time for Sample of unknown Final Boiling Point, Minutes | Test Result |
| A | 14.1 | 18.3 | Fail |
| B | 14.1 | 10.0 | Pass |

EXAMPLE 2

In order to compare the final boiling point of a gasoline sample found by the use of the apparatus and test described herein with the results found by an actual laboratory distillation such as ASTM D-86, the final boiling points for thirty gasoline samples were found by both methods. Determination of the actual final boiling point of an unknown sample via the test described herein requires finding retention times for two or three samples with known final boiling point and linearly interpolating. This is not normally necessary, but is done to compare the results obtained by the gas chromatographic method with those found by ASTM D86. The chromatographic tests were repeated on subsequent days to determine the reproducibility of the chromatographic method. The results of the comparison are present in Table 2.

Table 2

| Sample No. | ASTM D-86 FBP, °F | Portable Gas Chromatograph Day No. 1 FBP, °F | Portable Gas Chromatograph Day No. 2 FBP, °F |
|---|---|---|---|
| 1 | 400 | 395 | 400 |
| 2 | 418 | 421 | 423 |
| 3 | 416 | 415 | 415 |
| 4 | 405 | 418 | 400 |
| 5 | 399 | 396 | 404 |
| 6 | 378 | 370 | 383 |
| 7 | 363 | 365 | 365 |
| 8 | 422 | 421 | 423 |
| 9 | 422 | 418 | 419 |
| 10 | 425 | 421 | 433 |
| 11 | 404 | 410 | 392 |
| 12 | 392 | 390 | 390 |
| 13 | 388 | 384 | 398 |
| 14 | 378 | 378 | 386 |
| 15 | 384 | 385 | 377 |
| 16 | 398 | 380 | 410 |
| 17 | 388 | 389 | 387 |
| 18 | 378 | 371 | 385 |
| 19 | 381 | 389 | 379 |
| 20 | 360 | 364 | 350 |
| 21 | 362 | 361 | 361 |
| 22 | 374 | 377 | 391 |
| 23 | 426 | 422 | 428 |
| 24 | 428 | 431 | 425 |
| 25 | 421 | 415 | 425 |
| 26 | 420 | 420 | 420 |
| 27 | 419 | 424 | 414 |
| 28 | 396 | 399 | 397 |
| 29 | 420 | 427 | 415 |
| 30 | 422 | 420 | 424 |

Thus it is seen that the final boiling point of a sample which may be simply obtained by the use of the apparatus described herein correlates well with the boiling point found by the ASTM D-86 actual distillation test.

I claim:

1. An apparatus for measuring the retention time of a volatile liquid sample in a chromatographic column which comprises:
   a. a chromatograph of such resolution that the detector output signal exceeds a set point, hereinafter defined, during the elution of at least 98% of said sample from the column;
   b. a timer; and
   c. means for energizing the timer during the period in which the detector output signal exceeds the set point,
      said set point being greater than signals resulting from instrument and line noise, and less than the detector output signal during the elution of at least 98% of the sample from the column of the chromatograph.

2. The apparatus of claim 1 wherein said chromatograph comprises:
   a. a chromatographic column;
   b. means for creating a continuous flow of carrier gas through the column;
   c. a means for injecting a measured amount of said volatile liquid sample into the flow of carrier gas;
   d. means for volatilizing said sample prior to entry into the column; and
   e. means for detecting said sample eluted from the column.

3. The apparatus of claim 2 wherein said column comprises a hollow tube packed with a solid support, the surface of which is coated with a nonvolatile liquid.

4. The apparatus of claim 2 wherein said carrier gas is helium.

5. The apparatus of claim 2 further comprising means for maintaining said column at an isothermal temperature.

6. The apparatus of claim 5 wherein said maintaining means comprise a temperature controlled oven.

7. The apparatus of claim 5 wherein said isothermal temperature is selected from the range from about 250° F to about 350° F.

8. The apparatus of claim 2 wherein said detecting means comprises a thermal conductivity detector.

9. The apparatus of claim 2 wherein said flow of carrier gas comprises a rate from about 5 to about 10 liters/hour.

10. The apparatus of claim 2 wherein said injecting means comprise:
   a. a housing having therein a cavity and four passages extending from the cavity to the wall of the housing;
   b. a lower polymerized tetrafluoro ethylene seat positioned in the cavity;
   c. a ball having an aperture therethrough rotatably mounted on the lower polymerized tetrafluoro ethylene seat;
   d. a stem connected to said ball;
   e. an upper polymerized tetrafluoro ethylene seat; and
   f. means to provide contact between the ball and the upper and lower polymerized tetrafluoro ethylene seats to prevent leakage.

* * * * *